(12) United States Patent
Olson

(10) Patent No.: US 7,930,039 B2
(45) Date of Patent: Apr. 19, 2011

(54) IMPLANTABLE RETENTION SYSTEM AND METHOD

(75) Inventor: Robert L. Olson, Vadnais Heights, MN (US)

(73) Assignee: Medtronic, Inc., Minneapolis, MN (US)

(*) Notice: Subject to any disclaimer, the term of this patent is extended or adjusted under 35 U.S.C. 154(b) by 1232 days.

(21) Appl. No.: 11/328,297

(22) Filed: Jan. 9, 2006

(65) Prior Publication Data

US 2006/0173520 A1 Aug. 3, 2006

Related U.S. Application Data

(60) Provisional application No. 60/642,248, filed on Jan. 7, 2005.

(51) Int. Cl.
*A61N 1/05* (2006.01)

(52) U.S. Cl. ........ 607/126; 607/116; 607/118; 607/119; 607/130; 600/377; 600/386

(58) Field of Classification Search .................. 600/377, 600/386; 607/116, 118–119, 130, 126
See application file for complete search history.

(56) References Cited

U.S. PATENT DOCUMENTS

| | | | |
|---|---|---|---|
| 5,683,446 A | 11/1997 | Gates | |
| 5,746,722 A | 5/1998 | Pohndorf et al. | |
| 5,824,032 A | 10/1998 | Belden | |
| 5,938,596 A * | 8/1999 | Woloszko et al. | 600/377 |
| 5,957,968 A * | 9/1999 | Belden et al. | 607/126 |
| 6,036,673 A * | 3/2000 | Quinn | 604/178 |
| 6,397,108 B1 * | 5/2002 | Camps et al. | 607/115 |
| 6,901,287 B2 | 5/2005 | Davis et al. | |
| 7,223,256 B2 | 5/2007 | Bierman | |
| 7,247,150 B2 | 7/2007 | Bierman | |
| 2003/0220678 A1 | 11/2003 | Tronnes et al. | |

FOREIGN PATENT DOCUMENTS

| | | |
|---|---|---|
| EP | 1048320 B1 | 8/2005 |
| WO | WO03/092781 | 11/2003 |
| WO | WO03/099375 | 12/2003 |

* cited by examiner

*Primary Examiner* — Niketa I Patel
*Assistant Examiner* — Rex Holmes

(57) ABSTRACT

An implantable anchor for anchoring a lead or catheter relative to biological tissue, implantable system including such an anchor and a lead or catheter, and a method of use of such anchor. The anchor comprises a body having a channel adapted to receive a catheter or lead, and a cover mounted on the body for pivoting motion along a lateral axis, that is an axis that extends generally in the lateral direction perpendicular to the catheter or lead, between an open position in which the anchor is adapted to allow a lead or catheter to be placed in or moved along the channel, and a locked position in which the anchor is adapted to retain a lead or catheter within the channel.

16 Claims, 17 Drawing Sheets

IMPLANTABLE RETENTION SYSTEM AND METHOD

RELATED APPLICATION

This application claims priority to U.S. Provisional Application No. 60/642,248, filed Jan. 7, 2005. U.S. Provisional Application No. 60/642,248 is hereby incorporated herein by reference in its entirety.

FIELD

This application generally relates to implantable lead or catheter retention systems, and more particularly to retention systems that anchor medical electrical leads or drug delivery catheters to biological tissue.

BACKGROUND

Medical electrical leads or drug delivery catheters (hereafter referred to as therapy devices) are placed in the contact with biological tissue to delivery a therapy to the patient. These therapy devices are part of a system that may include signal or pulse generators (IPGs) or drug delivery pumps or combinations of such. The stimulators or pumps in the system may be external to, or implanted in, the patient.

Medical electrical leads may be used, for example, to delivery electrical energy to various biological tissues such as the heart, brain, or peripheral nervous system, etc. For example, implantable leads, such as the Medtronic Model 3487A lead, have been used for stimulating the dorsal columns of the spinal cord, or implantable leads, such as the Medtronic Model 3587A, have been used for peripheral nerve stimulation.

Medical drug delivery catheters, for example, may be used to delivery therapeutic agents to the intrathecal space of the spinal canal, or to the blood vasculature, or brain ventricles, etc. Catheters such as the Medtronic Model 8703 may be used for these types of applications.

Various lead or catheter anchors or retention systems are described in U.S. Pat. Nos. 5,683,446; 5,746,722; 5,824,032; 5,957,968 and 6,901,287; US published patent application Publication No. 2003/0220678; European Patent Publication No. 1,048,320; and PCT International Publication No. WO 03/099375.

BRIEF SUMMARY OF EXEMPLARY EMBODIMENTS

Examplary embodiments of the retention system serve to prevent therapy device migration after implantation of leads or catheters in the patient. Implantable neurostimulation or drug delivery systems are exemplified in this application for purposes of illustration, but one skilled in the art would realize that the concepts presented would be applicable to other medical devices such as heart pacemaker and defibrillators as well as other drug delivery methods.

In a first exemplary embodiment, an implantable anchor is provided for anchoring a lead or catheter relative to biological tissue. The anchor of the first exemplary embodiment generally comprises a body having a channel adapted to receive a catheter or lead, and a cover. The channel defines a longitudinal axis, and the cover is mounted on the body for pivoting motion, along a lateral axis generally perpendicular to the longitudinal axis, between: an open position in which the anchor is adapted to allow a lead or catheter to be placed in or moved along the channel, and a locked position in which the anchor is adapted to retain a lead or catheter within the channel.

In a second exemplary embodiment, a method is provided for anchoring an elongate medical device to biological tissue. The method of the second exemplary embodiment generally comprises providing an anchor having a body and a cover in which the cover is in an open position; placing the elongate medical device in a channel defined in the body of the anchor; pivoting the cover relative to the body, along an axis that is perpendicular to the longitudinal axis of the elongate medical device, to a locked position in which the cover presses against the elongate medical device; and suturing the anchor to biological tissue.

Exemplary embodiments of the retention systems prevent therapy device migration after implantation. Exemplary hinged cover may provide for zero, or near zero, insertion force when in the open position and sufficient device retention force when in the closed position. The hinged cover may also contain a locking mechanism to provide positive engagement with the body portion of the retention system.

Exemplary embodiments of the invention may provide: 1) zero or near-zero insertion force, 2) sufficient retention force, 3) gripping features on the internal surfaces of the hinged portion and the body portion of the retention device, 4) secure hinged portion closure features, 5) soft end caps to provide strain relief to prevent therapy device kinking and 6) positive closure features to engage hinged portion with body portion.

The exemplary lateral axis (i.e. an axis extending in the lateral direction, and not merely an axis displaced laterally from the longitudinal axis) may help provide a more generally uniform retention force along the circumference of the lead or catheter.

As used herein, the term, "exemplary" is used in the sense of for example or for purposes of illustration, and not in a limiting sense.

DETAILED DESCRIPTION OF THE EXEMPLARY EMBODIMENTS

Figure 1:
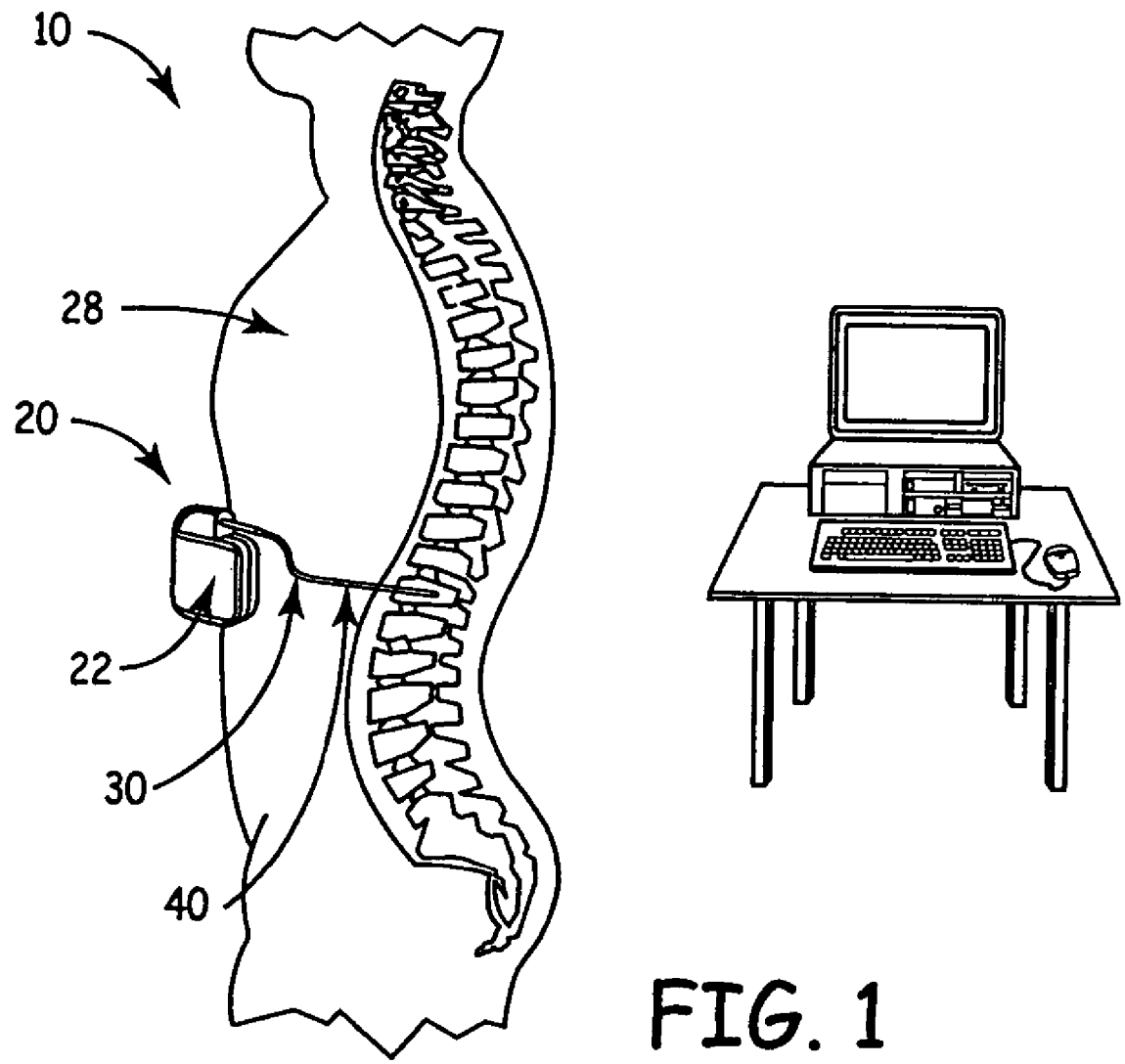
FIG. 1 shows a general environmental view for an exemplary embodiment of a neurostimulation or drug delivery system used to provide therapy to the spinal cord.
Figure 2:
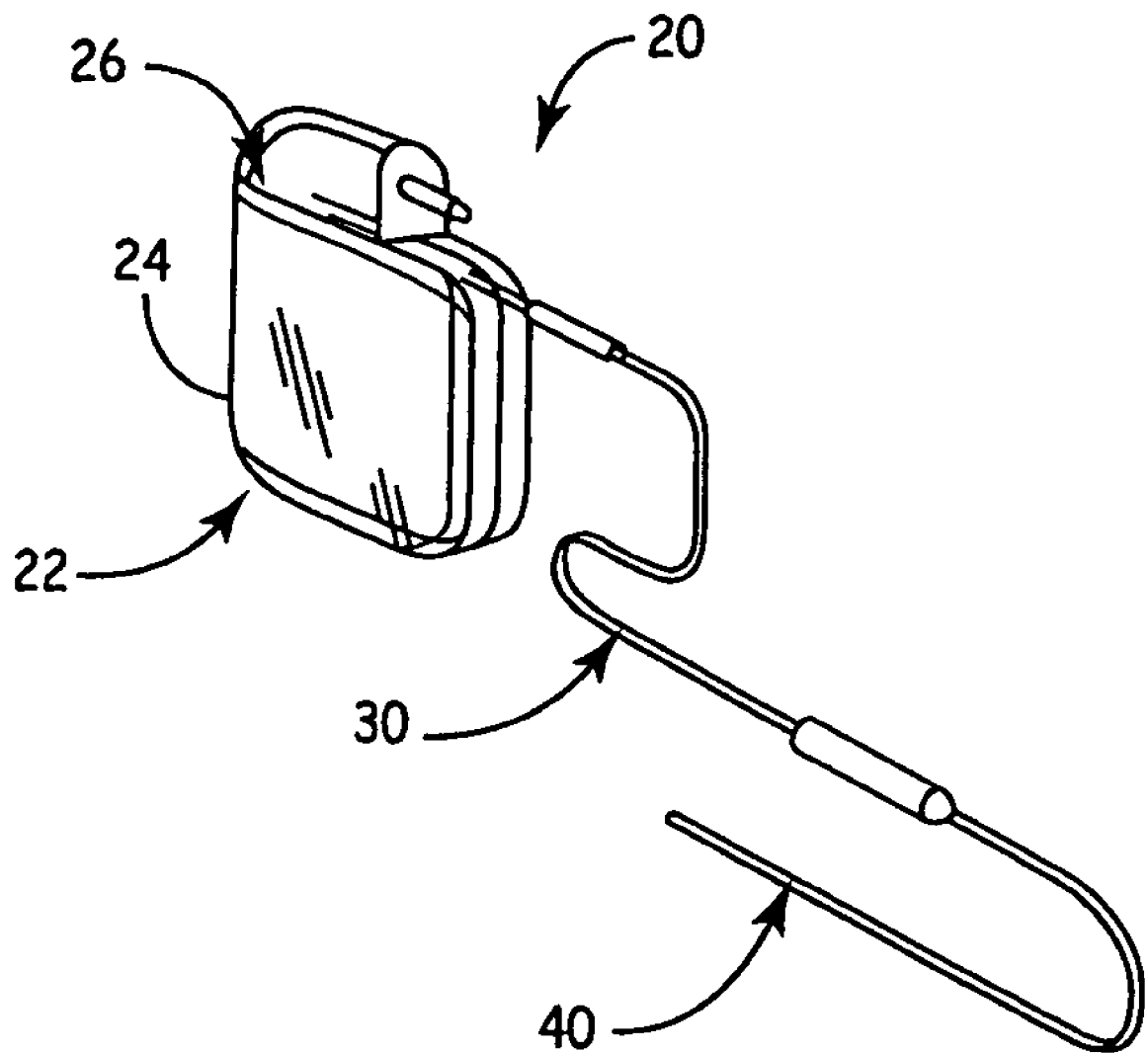
FIG. 2 shows the exemplary neurostimulation system of FIG. 1.

FIG. 1 shows a general environmental view 10 for an exemplary implantable neurostimulation system. Neurostimulation systems may be used to treat conditions such as pain, movement disorders, pelvic floor disorders, gastroparesis, and a wide variety of other medical conditions. As illustrated in FIGS. 1 and 2, the neurostimulation system 20 may include a neurostimulator 22, one or more stimulation lead extension(s) 30, and one or more stimulation lead(s) 40. The neurostimulator 22 is typically implanted subcutaneously in the patient's body 28 at a location selected by the clinician. The stimulation lead 40 is typically fixed in place near the location selected by the clinician using a device such as an adjustable anchor. Examples include placing the lead in the epidural space near the spinal cord, in or along the brain, or in muscle or subcutaneous tissue.

The exemplary implantable neurostimulator 22 has a housing, a power supply in the housing 24, and stimulation electronics in the housing in electrical communication with the battery and in electrical communication with a connector block 26, which may also be known as a terminal block.

Figure 3:
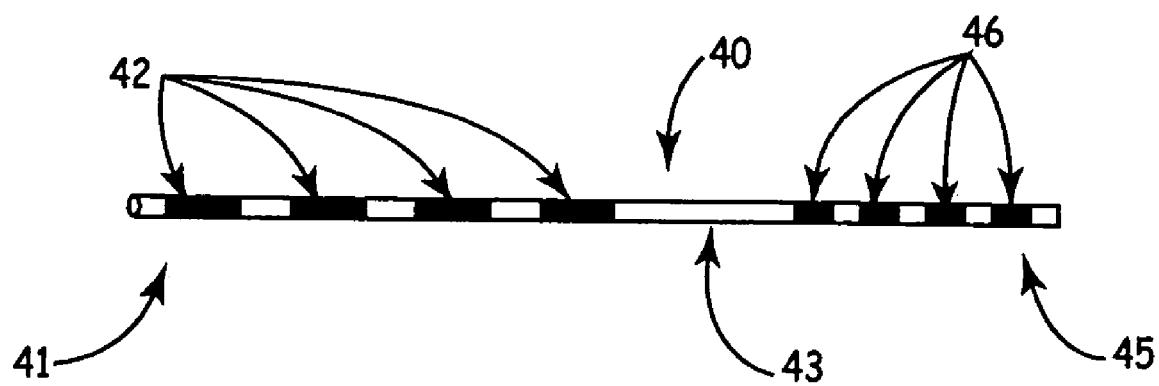
FIG. 3 shows the exemplary lead of FIGS. 1 and 2.

The exemplary stimulation lead 40 shown in FIG. 3, has a proximal end portion 45, a distal end portion 41 and a lead body 43 extending between the proximal end portion 45 and distal end portion 41. The proximal end portion 45 has at least one electrical connector 46 (also known as electrical terminals or contacts), with various standard pluralities, such as four or eight electrical contacts, being typical. The distal end portion 41 has at least one stimulation electrode 42, with various standard pluralities, such as four or eight electrodes, being typical.

There is at least one lead conductor 50 contained in the lead body 43 that is electrically connecting the electrical connector 46 to the stimulation electrode 42. Typically, at least one conductor may be used to establish electrical communication between a single electrical connector/electrode pair, although alternative examples include multiplexing or bus features within the lead to allow use of fewer conductors along the length of the lead than the number of electrodes. As used herein, "conductive means" or "means for electrical communication between electrodes and electrical connectors include the foregoing examples or any alternative structure to allow selection or electrical activation of one or more electrode.

Figure 4:
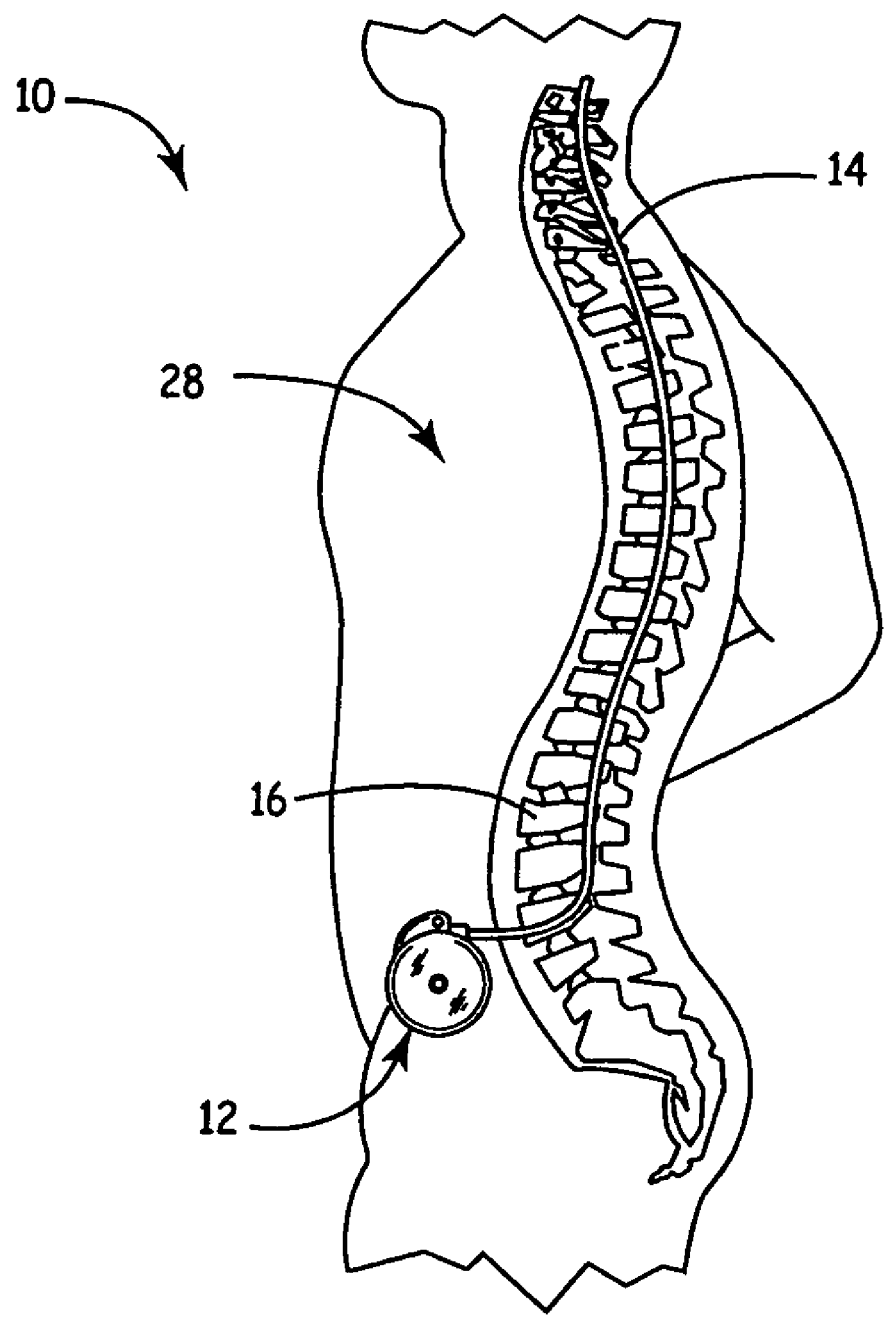
FIG. 4 shows an exemplary drug delivery environment.
Figure 5:
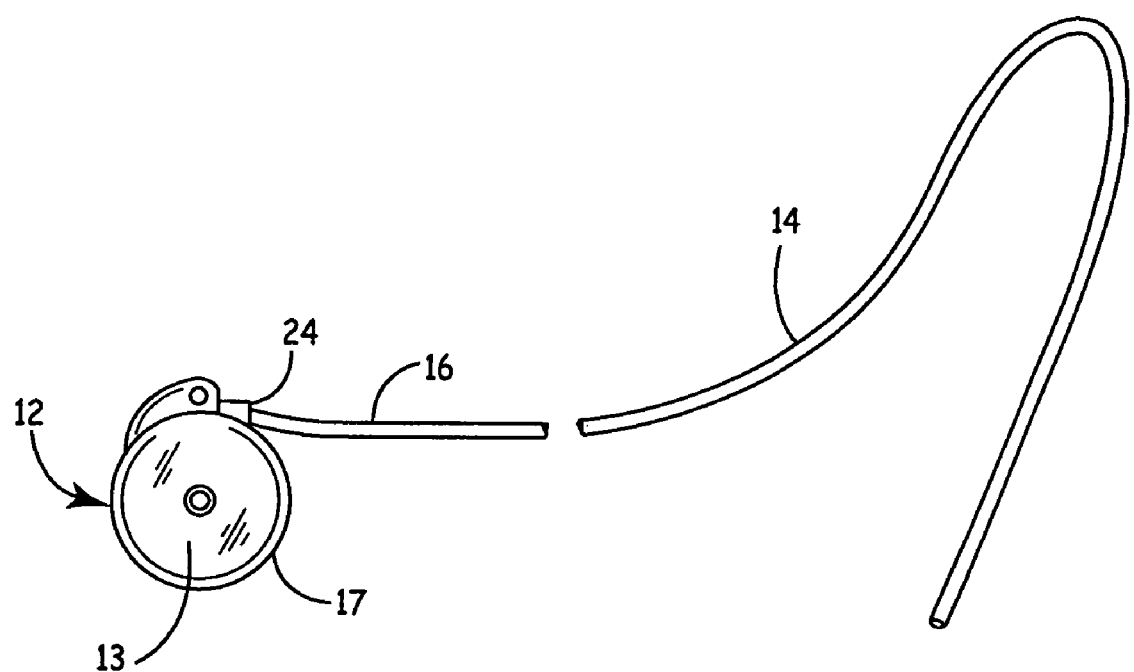
FIG. 5 shows an exemplary drug delivery system.

FIG. 4 shows a general environmental view 10 for an exemplary implantable drug delivery system embodiment. Drug delivery systems may be used to treat conditions such as pain, movement disorders, diabetes and a wide variety of other medical conditions. As illustrated in FIGS. 4 and 5, the drug delivery system 12 may include a drug delivery pump 13, a proximal catheter portion and a distal catheter portion 14. The drug pump 13 is typically implanted subcutaneously in the patient's body 28 at a location selected by the clinician. The distal catheter portion 14 is typically fixed in place near the location selected by the clinician using a device such as an adjustable anchor.

The exemplary implantable drug delivery pump 13 has a housing, a power supply in the housing 17, pumping mechanism and pump electronics in the housing. The pumping mechanism is in direct communication with the therapy delivery element through the connector 24 also part of the housing 17.

The therapy delivery element in a drug delivery system may include a distal catheter 14 and an optional proximal catheter 16. Both proximal catheter 16 and distal catheter 14 have a lumen therethough.

Figure 6:
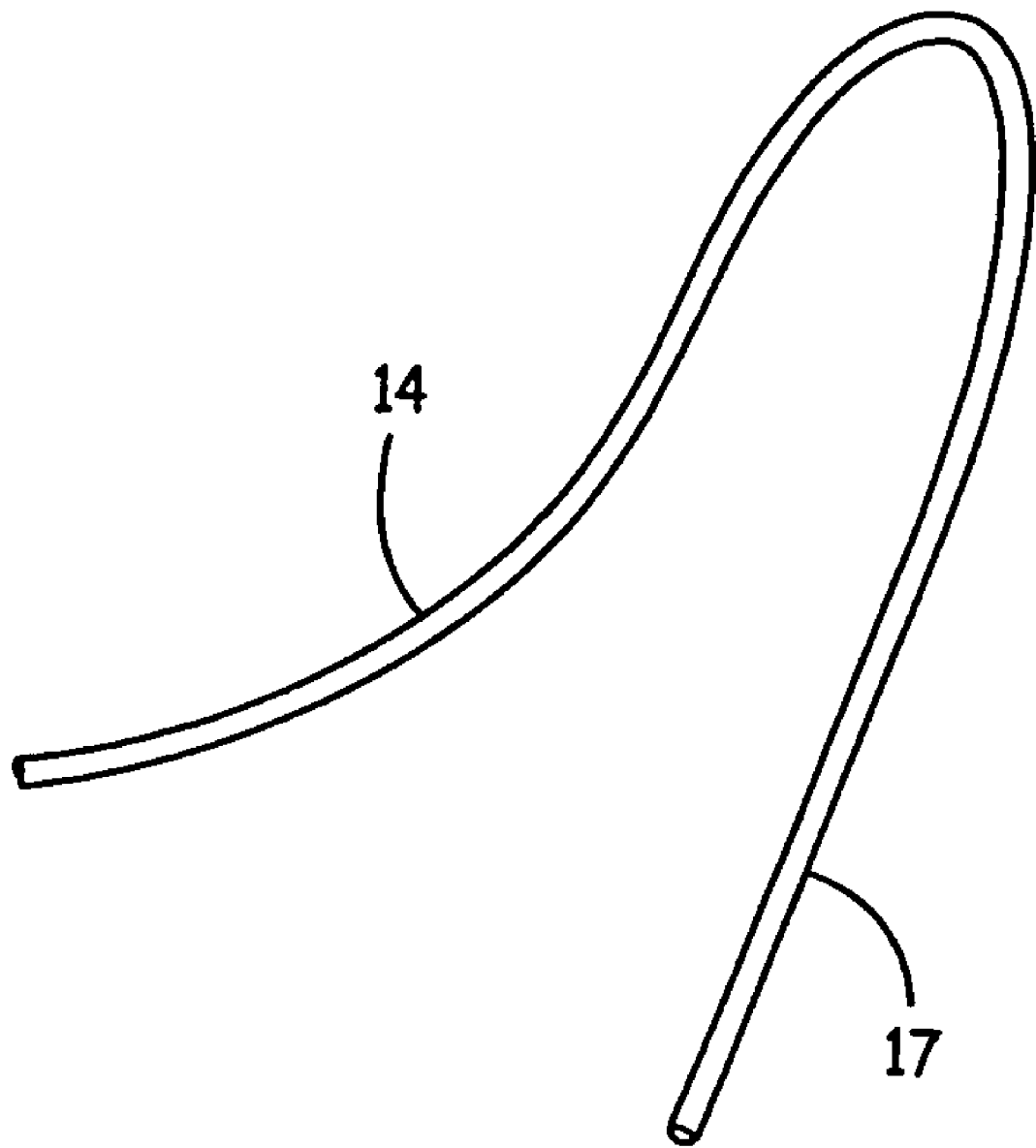
FIG. 6 shows the exemplary catheter of FIGS. 4 and 5.

FIG. 6 shows an exemplary distal catheter 14. The catheter is generally cylindrical in shape with lumen 18 therethrough. More that one lumen may be present in distal catheter 14. In addition, elements may be included in proximal catheter 14 to provide hoop strength to the device to prevent kinking or crushing.

A retention system using mechanical gripping may be used to prevent migration of the therapy delivery element after a therapy site has been chosen. Preferred exemplary embodiments of this invention use a hinged mechanism that provide compressive forces on the therapy delivery element when closed. An added benefit of the exemplary embodiments is a zero insertion force property. This property allows the retention system to be utilized with therapy deliver devices that may or may not have adequate structure to prevent buckling of therapy device while being inserted into the retention system. The system may also employ soft flexible ends to mitigate potential lead issues related to bending of the lead as it enters the fascia.

As illustrated in FIGS. 7-11, a first exemplary retention system or anchor 100 includes a body 110, a hinged portion or cover 120 and a proximal and distal soft portion 130. The body 110 has a lumen or channel (or preferably a combination of two lumens 108 and a channel 109) defining a longitudinal axis or direction, with the lumen and/or channels being adapted to receive a lead or catheter. The channel 109, and optionally the lumens 108, form(s) an exemplary embodiment of a means for receiving an elongate medical device (e.g., catheter or lead), with such receiving means defining a longitudinal axis.

The cover 102 is mounted on the body 110 for pivoting motion, along a lateral axis generally perpendicular to the longitudinal axis, between: an open position (e.g., FIG. 10) in which the anchor 100 is adapted to allow a lead or catheter to be placed in or moved along the channel 109 or lumens 108, and a locked position (e.g., FIG. 11) in which the anchor 110 is adapted to retain a lead or catheter within the channel 109 or lumens 108. For example, body 110 may have protrusions 111 that define a fixed pivot portion of a hinge with a hinge axis that is generally perpendicular (i.e. the lateral direction or lateral axis) to the longitudinal axis of the body 110. Hinged portion 120 has tab features 115 with holes 117 therethrough, which define the rotational portion of the hinge. The protrusions 111 on the body and tab features 115 with through holes constitute an exemplary embodiment of an axis means for providing an axis for pivotable motion that is generally perpendicular to the longitudinal axis defined by the receiving means (e.g., channel 109).

The hinged portion may also optionally include locking feature 124 that provide an interference interaction with the body portion 110. This interference may be in the form of a frictional fit or snap-fit/snap-lock, e.g., the body 110 may include an indentation to receive locking feature 124 providing secure closure of the hinged portion. Such features form a snap lock mechanism formed by the cover 120 and body 110 to retain the cover 120 in the locked position. The snap lock mechanism forms an exemplary embodiment of a means, or snap-lock means, for retaining the cover 120 in the locked position.

Figure 7:
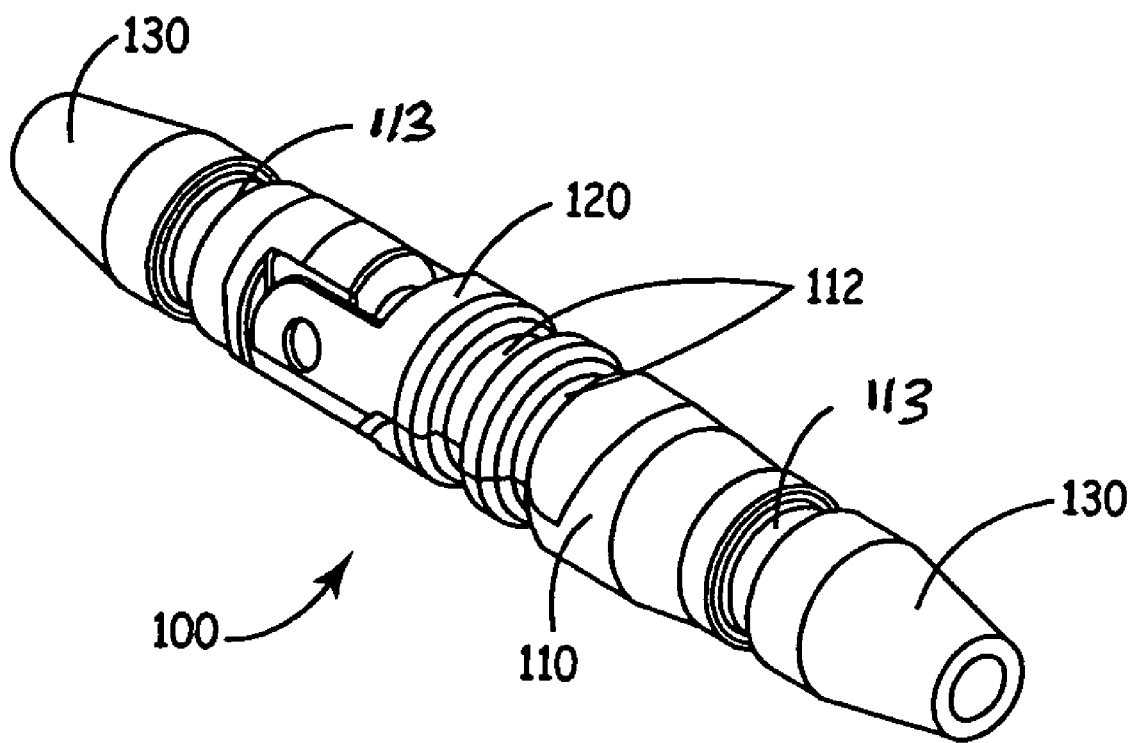
FIG. 7 shows the perspective view of a first exemplary embodiment of the anchor.

The body portion 110 also includes at least one suture-receiving groove 112 (two are shown in FIG. 7). The suture-receiving annular groove 112 may be formed along the cover 120 and the body 110 such that the cover 120 is adapted to be held in its locked position by tying a suture in the suture-receiving annular groove 112.

The body 110 and cover 120 may be formed of substantially rigid resin material. For example, the body 110 and hinged portion 120 may be formed of any suitable material, such as for example polycarbonate or polysulfone.

Figure 8:
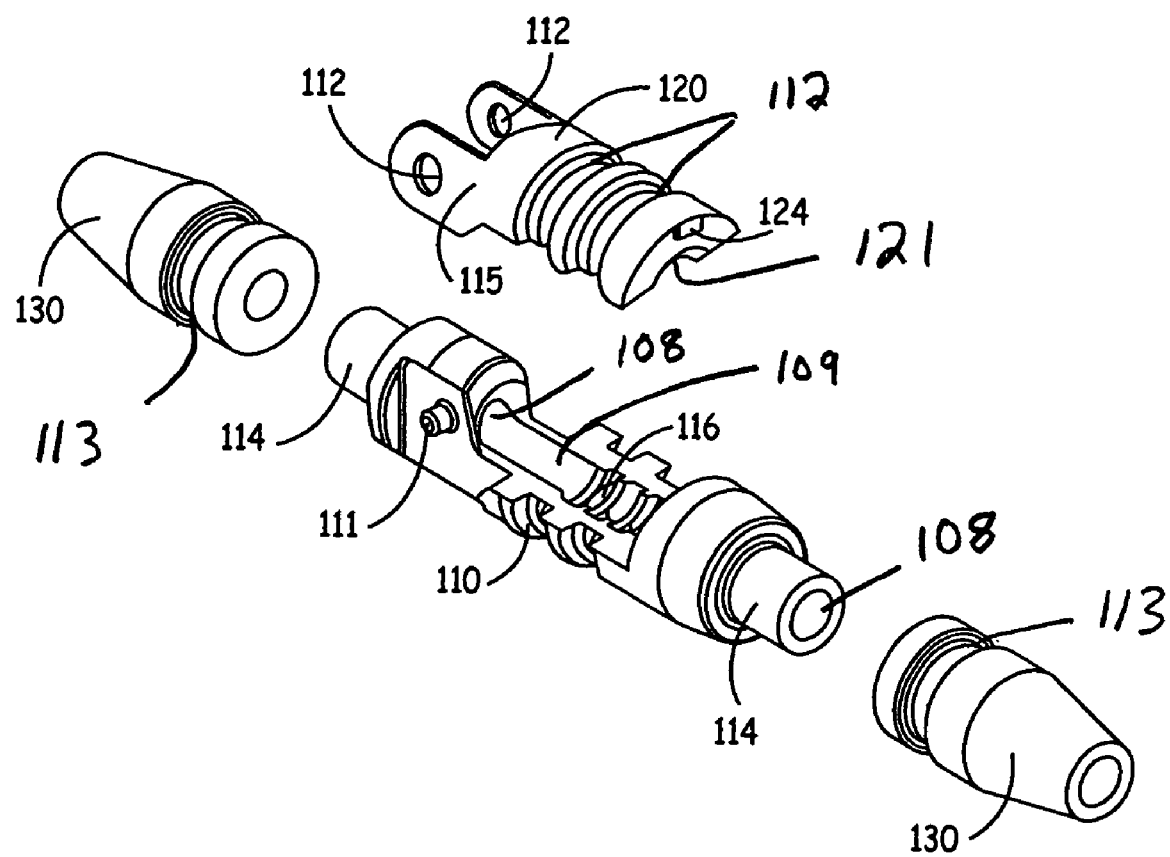
FIG. 8 shows an exploded view of the anchor of FIG. 7.
Figure 9:
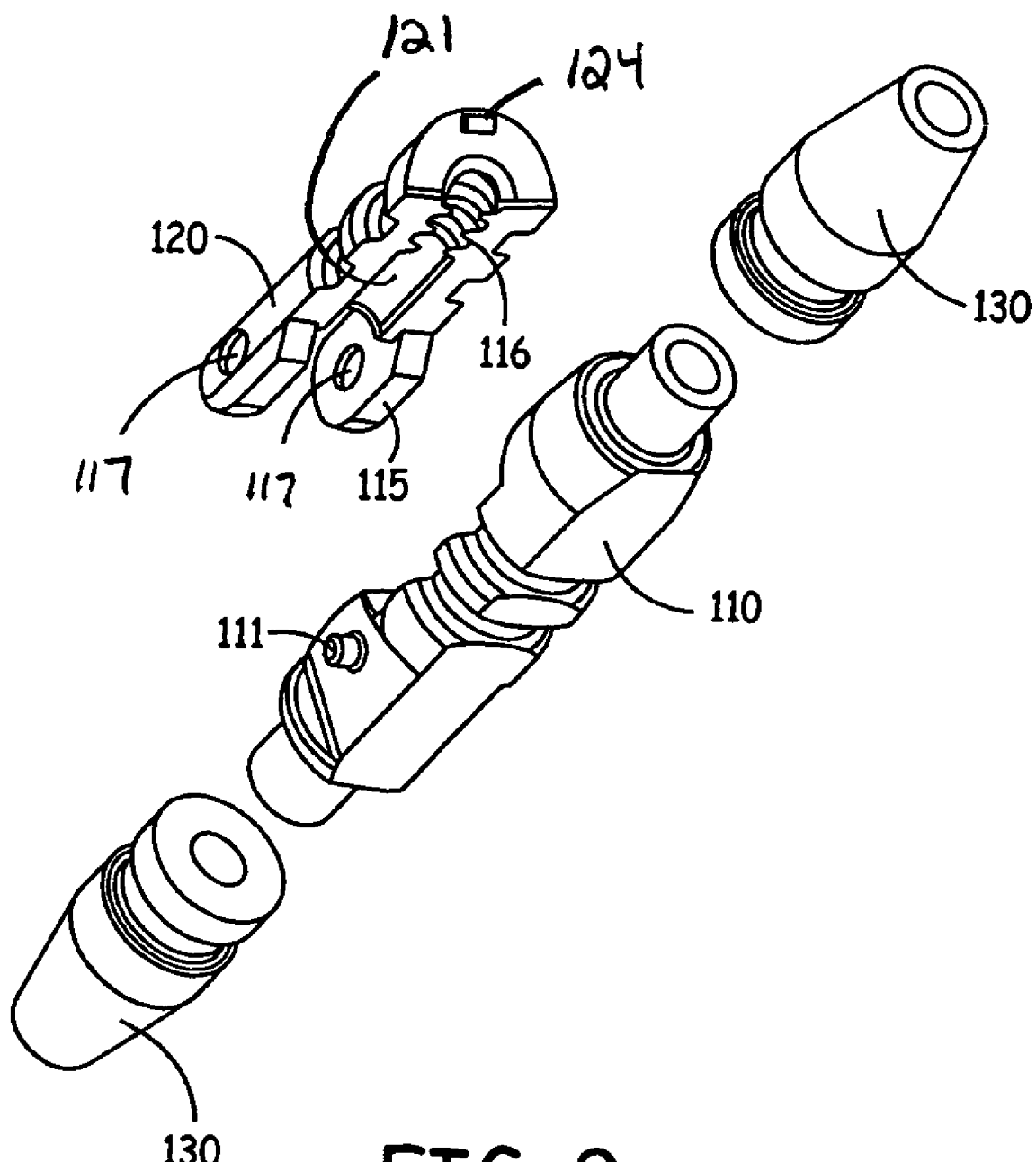
FIG. 9 shows an alternate exploded view of the anchor of FIGS. 7 and 8.

Soft, flexible ends 130 may be provided on the ends of the end caps 114. FIGS. 7 and 8 illustrate two such soft, flexible ends 130, one on each end. Such soft flexible ends may take the form, for example, of two tubular members 130 mounted on the body 110 and extending longitudinally from the body 110 in opposite directions. The flexible end 130 may be provided with suture-receiving grooves 113 (one shown in FIGS. 7 and 8 for each end). Soft end members 130 may be formed of any suitable material, such as elastomeric materials (e.g., silicone rubber or polyurethane).

The lumens 108 of the body 110 preferably are formed at opposite ends of the channel 109 and in alignment with the channel 109. The cover 120 preferably forms a channel 121 that aligns with the channel 109 of the body 110 to substantially to form a lumen in alignment with the lumens 108. Hinged portion 120 and body 110 have surface features 116, which may include grooves or threads, along the channel 109. Such surface features 116 may be formed to increase the retaining force on the lead or catheter.

Figure 10:
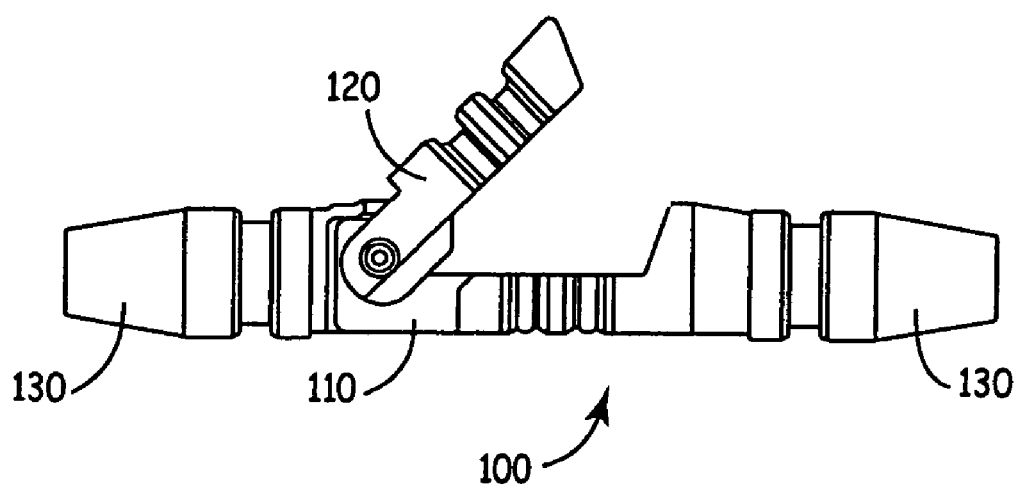
FIG. 10 shows a side view of the anchor of FIGS. 7-9 with the hinged portion or cover in the open position.

FIG. 10 shows a side view of the retention system 100 with the hinged portion 110 open. The retention system 100 is ready to receive a therapy delivery element (e.g., elongate medical device), such as a medical electrical lead of the types that may be used for electrical stimulation of tissue or monitoring/sensing, or a drug delivery catheter.

After the therapy delivery element is inserted through the retention system and the retention system is positioned to the practitioners liking, the hinged portion 120 is closed. Closure of the hinged portion 120 causes surface feature 116 to come into interference contact with the therapy delivery element. This interaction, in the form of compressive force, provides the retention force preventing therapy delivery element migration. When the hinged portion 120 is closed, optional locking feature 124 will interact with body 110. This interaction will provide an initial secure closure of the hinged portion and insure adequate compressive forces are applied. Once the hinged portion 120 is closed, sutures may be applied circumferentially about the retention system to prevent inadvertent opening of the hinged portion. In addition, the sutures are secured to the tissue fascia in the immediate vicinity of the retention system to prevent movement of the retention system.

Figure 11:
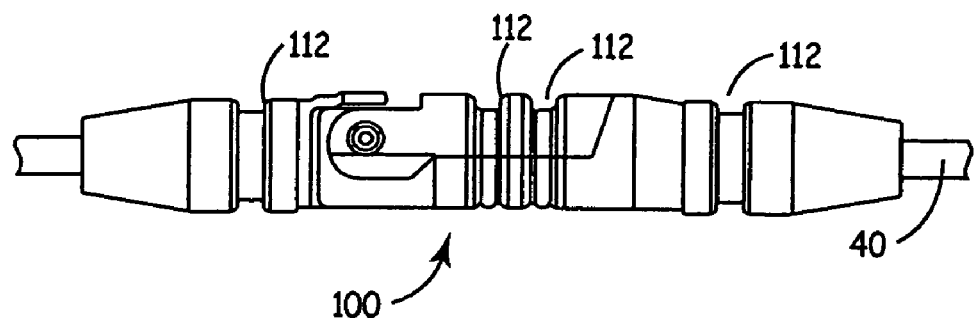
FIG. 11 shows a side view of the anchor of FIGS. 7-10 with the hinged portion or cover in the closed or locked position.
Figure 12:
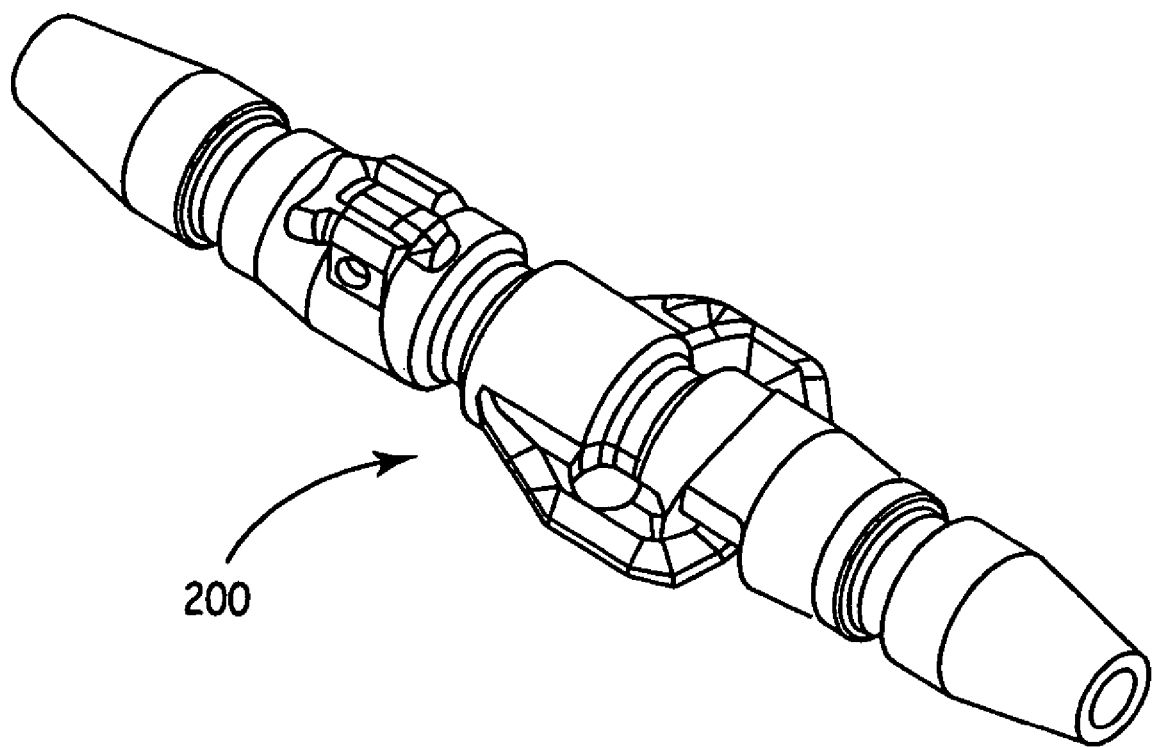
FIG. 12 shows a perspective view of a second exemplary embodiment of the anchor.
Figure 13:
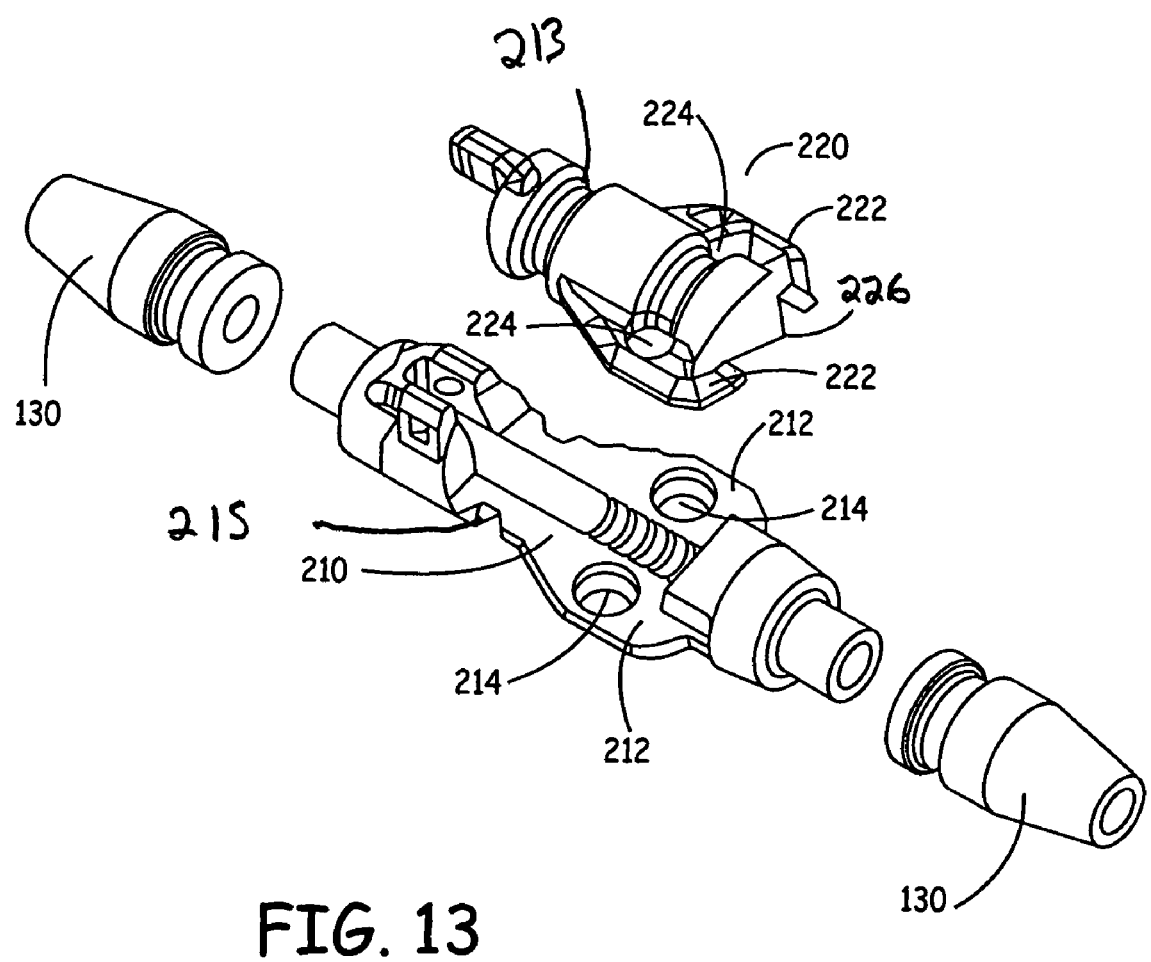
FIG. 13 shows an exploded view of the exemplary anchor of FIG. 12.
Figure 14:
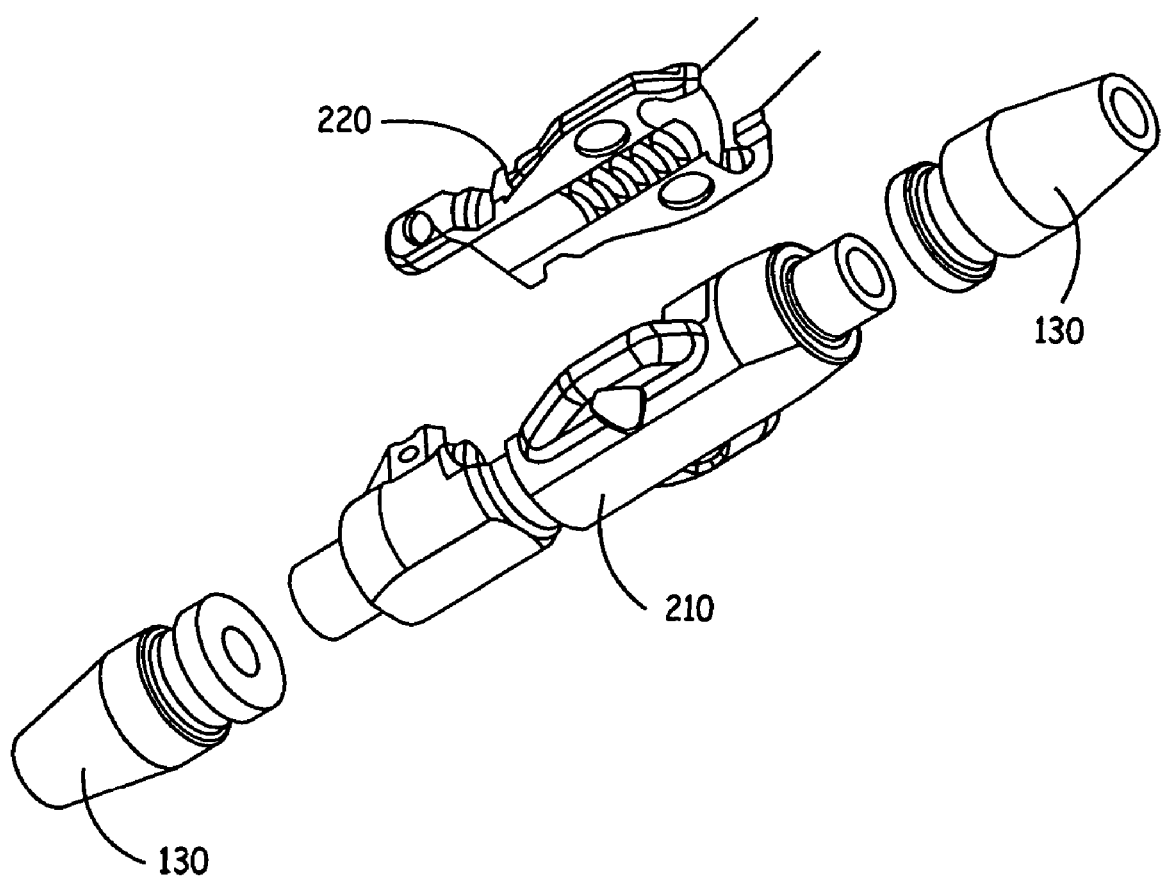
FIG. 14 shows an alternate exploded view of the exemplary embodiment of FIGS. 12 and 13.
Figure 15:
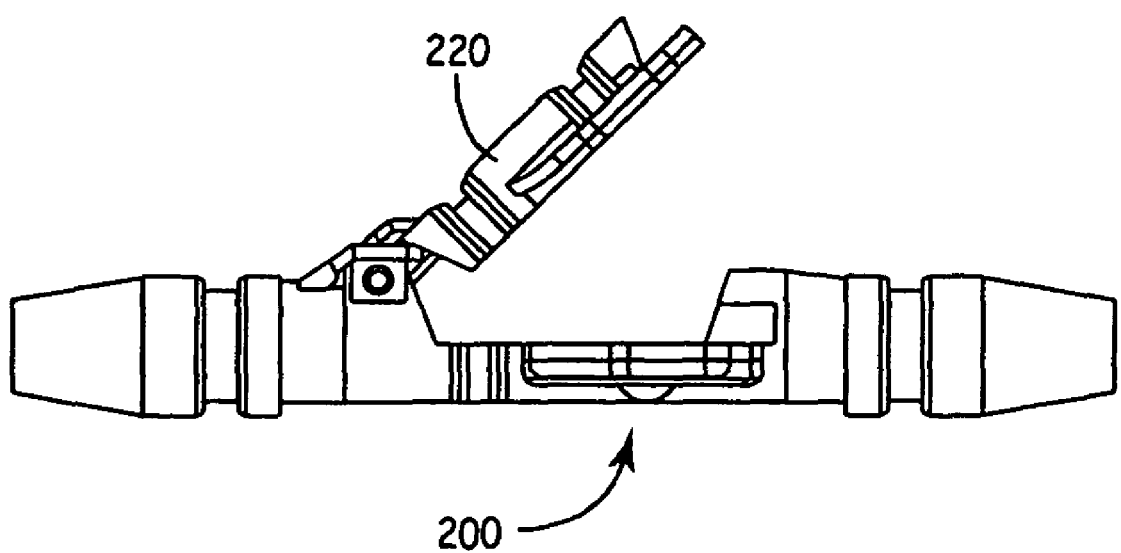
FIG. 15 shows a side view of the exemplary anchor of FIGS. 12-14 with the hinged portion or cover in the open position.
Figure 16:
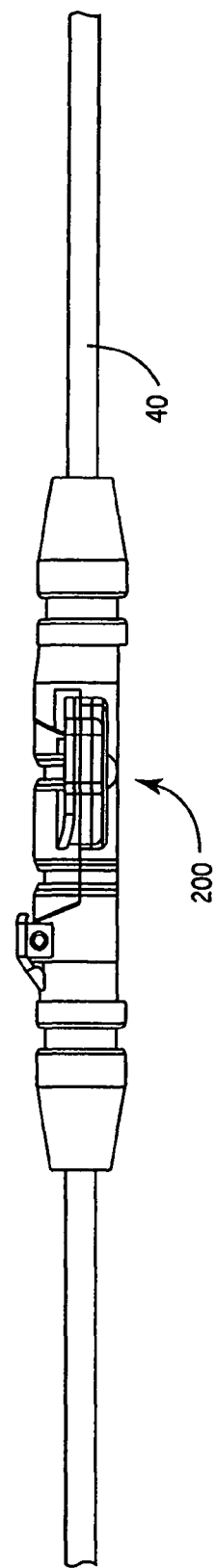
FIG. 16 shows a side view of the anchor of FIGS. 12-15 with the hinged portion or cover closed in the locked position, and lead engaged.

FIG. 11 shows the lead retention system engaging the therapy delivery element 40 (sutures not shown), with the cover 120 in the locked position.

FIGS. 12-16 illustrate a second exemplary embodiment of the retention system, now designated by the reference characters 200. Retention system 200 performs a similar function as retention system 100, and contains an additional element in the form of wings or flanges 212 and wings 222. Wings 212 are rigidly fixed to body 210 and provide a mating surface for wings 222 rigidly fixed to hinged portion or cover 220. When hinged portion 220 is closed to actuate therapy delivery element retention, wings 222 contact wings 212.

Tabs 226 on wings 222 alternately engage wings 212 to provide initial secure closure of hinged portion 220. The tabs 226 may be in the form of deflectable locking arms 226 on the cover 220, with the deflectable locking arms 226 being adapted to snap over the flange 212 as the cover 220 is moved to its locked position (e.g., FIG. 16) to retain the cover in its closed position. The tabs 226 form a second exemplary snap lock mechanism formed by the cover 220 and body 210 to retain the cover 220 in the locked position. The foregoing exemplary snap lock mechanism forms a second embodiment of a means, or snap-lock means, for retaining the cover in the locked position.

Hinged portion 220 and body 210 contain holes therethrough. Holes 224 align with holes 214 when the hinged portion 220 is closed (i.e. in the locked position). Sutures may be placed through the now aligned holes 214 and 224 to provide secure closure of hinged portion 220 insuring adequate compressive force is placed on the therapy delivery element and to prevent inadvertent opening of the hinged portion. In addition, suture may be placed circumferentially around the retention system to provide additional secure closure of the hinged portion.

Figure 17:
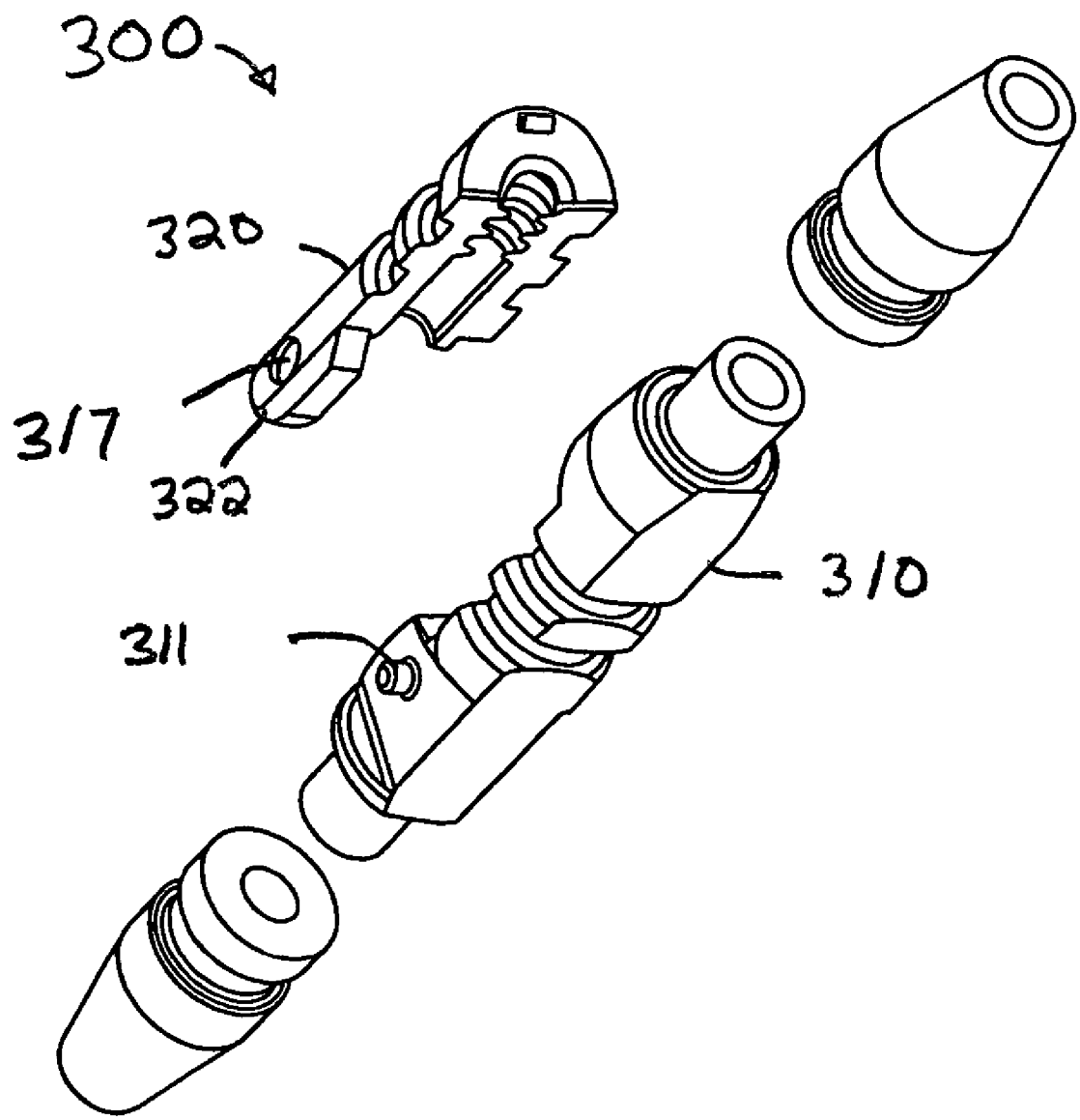
FIG. 17 shows an exploded view of third exemplary embodiment of the anchor with a swivel portion.

FIG. 17 illustrates a third exemplary embodiment similar in many respects to the first embodiment illustrated in FIGS. 7-11. In this embodiment, the anchor 300 includes a cover 320 that includes a single flange 322 with a single rotation-axis defining through hole 317, which receives a single protrusion 311 on the body 310 of the anchor 300. The through hole 317 and protrusion 311 constitutes an alternative exemplary embodiment of an axis means for providing an axis for pivotable motion that is generally perpendicular to the longitudinal axis defined by the receiving means. In an optional version of this exemplary embodiment, the through hole 317 and protrusion 311 may be configured to allow pivoting and swiveling motion to allow the benefits of the lateral rotational axis to be combined with the benefits of a swivel.

The anchor 100, 200 or 300 may be used in exemplary methods of anchoring an elongate medical device (e.g., catheter or lead) to biological tissue. With the cover in the open position, the elongate medical device may be placed in the channel 109 defined in the body of the anchor. The cover 120, 220, 320 may then be pivoted relative to the body 110, 210, 310, along the lateral axis, to a locked position (e.g., FIGS. 11 and 17) in which the cover 120, 220, 320 presses against the elongate medical device.

The cover may optionally be locked in its locked position with a snap lock mechanism formed by the cover and body, such as by use of features 124 or 226. For example, the cover may be locked in its locked position by deflecting locking arms 226 on the cover 220 over a flange 212 on the body 210 such that the locking arms 226 being snap over the flange 212 as the cover 220 is moved to its locked position The anchor may then be sutured to biological tissue using any or all of the suture-related features described with respect to the various exemplary embodiments. For example, a suture-receiving through hole 224 of the cover 220 may be moved into alignment with a suture-receiving through hole 214 of the body 210 when the cover 220 is moved to its locked position (e.g., FIG. 17) as the cover 220 is pivoted relative to the body 210 to the locked position. Another example includes tying at least one suture along a suture-receiving annular groove 112 formed by the cover 120 and the body 110 such that the cover 120 is held in its locked position by the suture. It will be appreciated that the two foregoing examples could optionally be combined in a single device, such as by using suture receiving grooves 213 and 215 on the cover 220 and body 210, respectively. Sutures may also be placed along the suture receiving grooves 113 of the soft end members 130.

Thus, embodiments of the implantable electrical lead retention system, implantable anchor, implantable system and method are disclosed. The disclosed embodiments are presented for purposes of illustration and not limitation.

What is claimed is:

1. An implantable anchor for anchoring a lead or catheter relative to biological tissue, the anchor comprising:
   a body having a channel adapted to receive a catheter or lead, the channel defining a longitudinal axis, the channel maintaining the longitudinal axis from an opening on one end of the body to an opening on another end of the body;
   a cover mounted on the body such that the cover pivots on a lateral axis generally perpendicular to the longitudinal axis and between:
      an open position in which the anchor is adapted to allow a lead or catheter to be placed in or moved along the channel, and
      a locked position in which the anchor is adapted to retain a lead or catheter within the channel.

2. The implantable anchor of claim 1 further comprising a snap lock mechanism formed by the cover and body to retain the cover in the locked position.

3. The implantable anchor of claim 2 wherein the snap lock mechanism includes:
   a flange on the body; and
   deflectable locking arms on the cover, the deflectable locking arms being adapted to snap over the flange as the cover is moved to its locked position to retain the cover in its closed position.

4. The implantable anchor of claim 3 wherein at least one suture-receiving through hole is formed in each of the cover and the body such that the suture-receiving through hole of the cover is in alignment with the suture-receiving through hole of the body when the cover is in its locked position.

5. The implantable anchor of claim 1 wherein at least one suture-receiving annular groove is formed along the cover and the body such that the cover is adapted to be held in its locked position by tying a suture in the suture-receiving annular groove.

6. The implantable anchor of claim 1 wherein the body is formed of substantially rigid resin material, the implantable anchor further including two tubular members mounted on the body and extending longitudinally from the body in opposite directions, the tubular members being substantially elastomeric.

7. An implantable system comprising:
   an elongate medical device selected from the group consisting of an implantable medical lead for electrically stimulating or sensing tissue and an implantable catheter for delivering therapeutic substances, such as drugs or biologics; and
   an implantable anchor for anchoring the elongate medical device relative to the biological tissue, the anchor comprising:
   a body having a channel for receiving the elongate medical device, the channel defining a longitudinal axis and the body providing protrusions defining a lateral axis; and
   a cover mounted on the body such that the cover pivots on the lateral axis about the protrusions and generally perpendicular to the longitudinal axis and between:
      an open position in which the anchor allows the elongate medical device to be placed in or moved along the channel, and
      a locked position in which the anchor is retains the elongate medical device within the channel.

8. The implantable system of claim 7 further comprising a snap lock mechanism formed by the cover and body to retain the cover in the locked position.

9. The implantable system of claim 8 wherein the snap lock mechanism includes:
   a flange on the body; and
   deflectable locking arms on the cover, the deflectable locking arms being adapted to snap over the flange as the cover is moved to its locked position to retain the cover in its closed position.

10. The implantable system of claim 9 wherein at least one suture-receiving through hole is formed in each of the cover and the body such that the suture-receiving through hole of the cover is in alignment with the suture-receiving through hole of the body when the cover is in its locked position.

11. The implantable system of claim 7 wherein at least one suture-receiving annular groove is formed along the cover and the body such that the cover is adapted to be held in its locked position by tying a suture in the suture-receiving annular groove.

12. The implantable system of claim 7 wherein the body is formed of substantially rigid resin material, the implantable anchor further including two tubular members mounted on the body and extending longitudinally from the body in opposite directions, the tubular members being substantially elastomeric.

13. The implantable system of claim 7 wherein the elongate medical device is an implantable medical lead for electrically stimulating or sensing tissue.

14. The implantable system of claim 13 further comprising an implantable pulse or signal generator electrically coupled with the implantable medical lead.

15. An implantable anchor for anchoring an elongate medical device relative to biological tissue, the anchor comprising:
   a body having receiving means for receiving the elongate medical device, the receiving means defining a longitudinal axis and including surface features;
   axis means for providing an axis for pivotable motion that is generally perpendicular to the longitudinal axis defined by the receiving means; and
   a cover mounted on the body via the axis means such that the cover pivots on a lateral axis and between:
      an open position in which the anchor is adapted to allow the elongate medical device to be placed in or moved along the receiving means, and
      a locked position in which the anchor is adapted to retain the elongate medical device within the receiving means by creating contact of the surface features to the elongate medical device.

16. An implantable anchor for anchoring a lead or catheter relative to biological tissue, the anchor comprising:
   a body having a channel adapted to receive a catheter or lead, the channel defining a longitudinal axis, the body further having a lumen on each end of the channel each lumen sharing the longitudinal axis of the channel; and
   a cover mounted on the body such that the cover pivots on a lateral axis generally perpendicular to the longitudinal axis and between:
      an open position in which the anchor is adapted to allow a lead or catheter to be placed in or moved along the channel and the lumen, and
      a locked position in which the anchor is adapted to retain a lead or catheter within the channel and the lumen.

* * * * *